United States Patent
Iriyama et al.

(10) Patent No.: US 9,101,564 B2
(45) Date of Patent: Aug. 11, 2015

(54) HEPARANASE ACTIVITY INHIBITOR, WRINKLE IMPROVING AGENT CONTAINING SAME, AND PHARMACEUTICAL COMPOSITION

(75) Inventors: Shunsuke Iriyama, Yokohama (JP); Hirotada Fukunishi, Yokohama (JP); Masaru Suetsugu, Yokohama (JP); Satoshi Amano, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 253 days.

(21) Appl. No.: 13/261,236

(22) PCT Filed: Sep. 29, 2010

(86) PCT No.: PCT/JP2010/066997
§ 371 (c)(1),
(2), (4) Date: Mar. 27, 2012

(87) PCT Pub. No.: WO2011/040495
PCT Pub. Date: Apr. 7, 2011

(65) Prior Publication Data
US 2012/0184782 A1    Jul. 19, 2012

(30) Foreign Application Priority Data
Sep. 30, 2009  (JP) .................... 2009-228209

(51) Int. Cl.
*A61K 8/00* (2006.01)
*A61K 31/05* (2006.01)
*A61K 8/34* (2006.01)
*A61Q 19/08* (2006.01)

(52) U.S. Cl.
CPC .............. *A61K 31/05* (2013.01); *A61K 8/347* (2013.01); *A61Q 19/08* (2013.01); *A61K 2800/782* (2013.01)

(58) Field of Classification Search
CPC ....... A61K 8/347; A61Q 19/08; C07D 311/60
USPC .............. 424/78.03; 568/766; 514/18.6, 18.7, 514/18.8
See application file for complete search history.

(56) References Cited

U.S. PATENT DOCUMENTS

| | | |
|---|---|---|
| 4,959,393 A | 9/1990 | Torihara et al. |
| 5,614,178 A * | 3/1997 | Bloom et al. ............... 424/60 |

FOREIGN PATENT DOCUMENTS

| EP | 0 341 664 A1 | 11/1989 |
|---|---|---|
| JP | 02-049715 A | 2/1990 |
| JP | 02-292213 A | 12/1990 |
| JP | 07-206669 A | 8/1995 |
| JP | 2001-302505 A | 10/2001 |
| JP | 2006-016343 A | 1/2006 |
| JP | 2006-124358 A | 5/2006 |
| JP | 2007-509966 A | 4/2007 |
| JP | 2007-254412 A | 10/2007 |
| WO | WO 2005/042712 A2 | 5/2005 |
| WO | WO 2009/122540 A1 | 10/2009 |
| WO | WO 2009/123215 A1 | 10/2009 |

OTHER PUBLICATIONS

Ilan et al., "Regulation, function and clinical significance of heparanase in cancer metastatis and angiogenesis," The International Journal of Biochemistry & Cell Biology, 2006, 38:2018-2039.
Vlodavsky et al., "Mammalian heparanase: involvement in cancer metastasis, angiogenesis and normal development," Cancer Biology, 2002, 12:121-129.
Zcharia et al., "Heparanase accelerates wound angiogenesis and wound healing in mouse and rat models," The FASEB Journal, Feb. 2005, 19:211-221.
Lipkin, E. Alfred, "Hexylresorcinol in the Treatment of Arthritis," The Lancet, Letters to the Editor, Aug. 24, 1957, 385-386.

\* cited by examiner

*Primary Examiner* — Sudhakar Katakam
*Assistant Examiner* — Pancham Bakshi
(74) *Attorney, Agent, or Firm* — Foley & Lardner LLP

(57) ABSTRACT

A heparanase activity inhibitor containing, as an active ingredient, a 4-alkylresorcinol represented by formula (I):

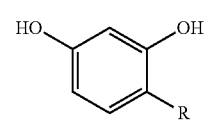

wherein R represents a C1-6 linear or branched alkyl group.

7 Claims, 6 Drawing Sheets

F I G.4
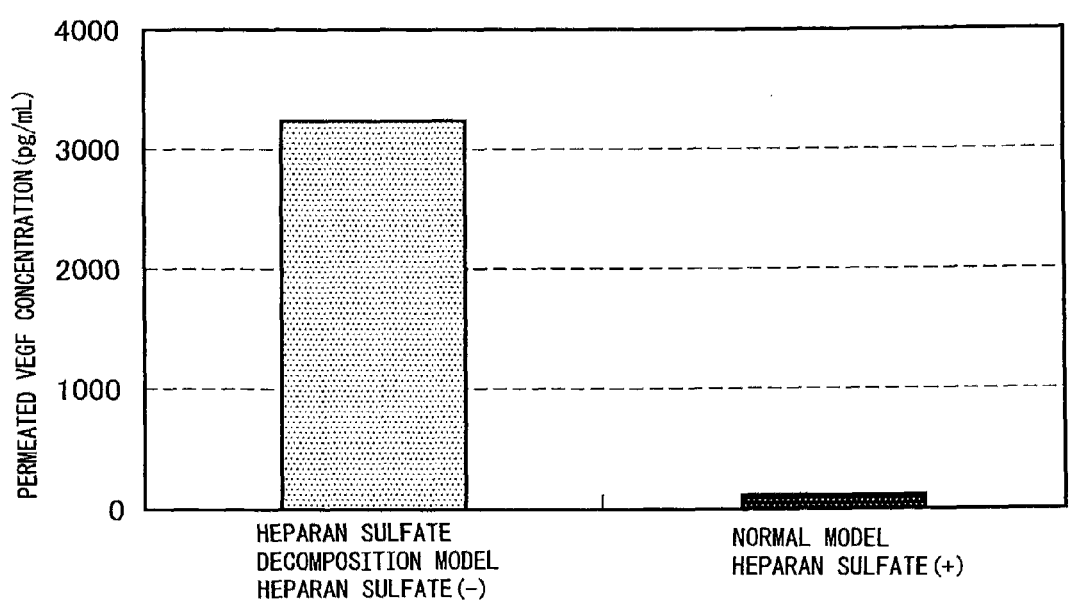

HEPARANASE ACTIVITY INHIBITOR, WRINKLE IMPROVING AGENT CONTAINING SAME, AND PHARMACEUTICAL COMPOSITION

CROSS-REFERENCE TO RELATED APPLICATIONS

This application is a National Stage application of PCT/JP2010/066997, filed Sep. 29, 2010, which claims priority from Japanese application JP 2009-228209, filed Sep. 30, 2009.

TECHNICAL FIELD

The present invention relates to a heparanase activity inhibitor containing a 4-alkylresorcinol as an active ingredient, and to a wrinkle improving agent and a pharmaceutical composition employing the heparanase activity inhibitor.

BACKGROUND ART

Heparanase is present in a variety of cells such as platelets, leukocytes, endothelial cells and smooth muscle cells, as an enzyme that specifically degrades heparan sulfate chains in various types of heparan sulfate proteoglycan. In the skin, in particular, it is produced by epidermal keratinocytes composing the epidermis and fibroblasts or vascular endothelial cells of the dermis. Its production is also known to be elevated in various types of cancer cells.

Heparan sulfate proteoglycan (HSPG), which is degraded by heparanase, is a polymer found in various animal tissue cell surfaces and extracellular matrices, and it is known to have functions including extracellular buildup of heparan sulfate-binding growth factors (bFGF (basic fibroblast growth factor), HGF (hepatocyte growth factor), VEGF (vascular endothelial growth factor), HB-EGF (heparin binding EGF-like growth factor), and the like).

Perlecan, a type of heparan sulfate proteoglycan, is also present in the epidermal basal membrane at the interface between the epidermis and dermis, and it binds heparan sulfate-binding growth factors to the epidermal basal membrane, controlling migration of growth factors between the epidermis and dermis. Perlecan also controls growth factors for epidermal basal cells that bind to the basal membrane, and it has been shown to be essential for proper growth and differentiation of the epidermis. Consequently, decomposition of perlecan heparan sulfate chains by activation or accelerated expression of heparanase disturbs release of accumulated growth factors and control of growth factors in the epidermis and dermis, leading to failure of control of differentiation and growth of the epidermis and thickening of the dermis, and promoting formation of wrinkles (see PCT/JP2009/056717). In other words, inhibition of heparanase activity suppresses the release of growth factors that accompanies decomposition of heparan sulfate, and allows migration of growth factors between the epidermis and dermis to be controlled, thereby aiding in anti-aging of the skin.

A link between heparanase and cancer malignancy has also been suggested. In particular, it is known that cancer cells with increased production of heparanase have higher proliferative and metastatic ability, and increased inducibility of angiogenesis (Non-patent document 1). Heparanase is also known to have a function of accelerating wound healing (Non-patent document 2). Therefore, effective inhibition of heparanase activity is effective for purposes including suppressing proliferation or metastasis of cancer cells, and suppressing angiogenesis.

PRIOR ART DOCUMENTS

Non-Patent Documents

Non-patent document 1: Vlodaysky I., et al., Semin Cancer Biol., 2002; 12(2):121-129
Non-patent document 2: Zacharia E., et al., FASEB J. 2005 February; 19(2):211-21

SUMMARY OF THE INVENTION

Problems to be Solved by the Invention

In light of the background explained above, it has been a goal to find substances that can effectively inhibit heparanase activity.

It is an object of the present invention, which has been accomplished in consideration of the above, to provide a heparanase activity inhibitor that can effectively inhibit heparanase activity, and a wrinkle improving agent and a pharmaceutical composition employing the heparanase activity inhibitor.

Means for Solving the Problems

As a result of much diligent research, the present inventors found that certain 4-alkylresorcinols effectively inhibit heparanase activity.

Specifically, the gist of the present invention is as follows.
(1) A heparanase activity inhibitor containing, as an active ingredient, a 4-alkylresorcinol represented by formula (I):

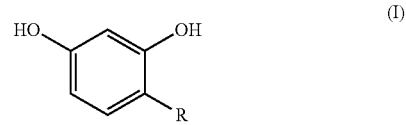

wherein R represents a C1-6 linear or branched alkyl group.
(2) A heparanase activity inhibitor according to (1), wherein R in formula (I) is a C2-4 linear or branched alkyl group.
(3) A heparanase activity inhibitor according to (2), wherein the 4-alkylresorcinol of formula (I) is 4-isobutylresorcinol.
(4) A pharmaceutical composition for treatment, improvement or prevention of a condition or symptom associated with heparanase activity, the pharmaceutical composition containing, as an active ingredient, a heparanase activity inhibitor according to any one of (1) to (3).
(5) A pharmaceutical composition according to (4), which is used for wound healing, suppression of proliferation or metastasis of cancer cells, or suppression of angiogenesis.
(6) A wrinkle improving agent that prevents or suppresses formation of wrinkles, the wrinkle improving agent containing, as an active ingredient, a heparanase activity inhibitor according to any one of (1) to (3).

Effect of the Invention

Since the heparanase activity inhibitor of the invention can efficiently inhibit heparanase activity, it can be suitably used, for example, as an active ingredient in a wrinkle improving agent, to prevent or suppress formation of wrinkles (particu-

BRIEF DESCRIPTION OF THE DRAWINGS

FIG. 3(a) shows a "heparan sulfate-decomposed model" (heparan sulfate (−)) with no heparan sulfate present in the basal membrane sheet, while FIG. 3(b) shows a "normal model" (heparan sulfate (+)) with heparan sulfate present in the basal membrane sheet;

FIG. 4 is a graph showing evaluation results for VEGF permeability using the pseudo-skin models of FIGS. 3(a) and 3(b);

BEST MODE FOR CARRYING OUT THE INVENTION

Figure 1:
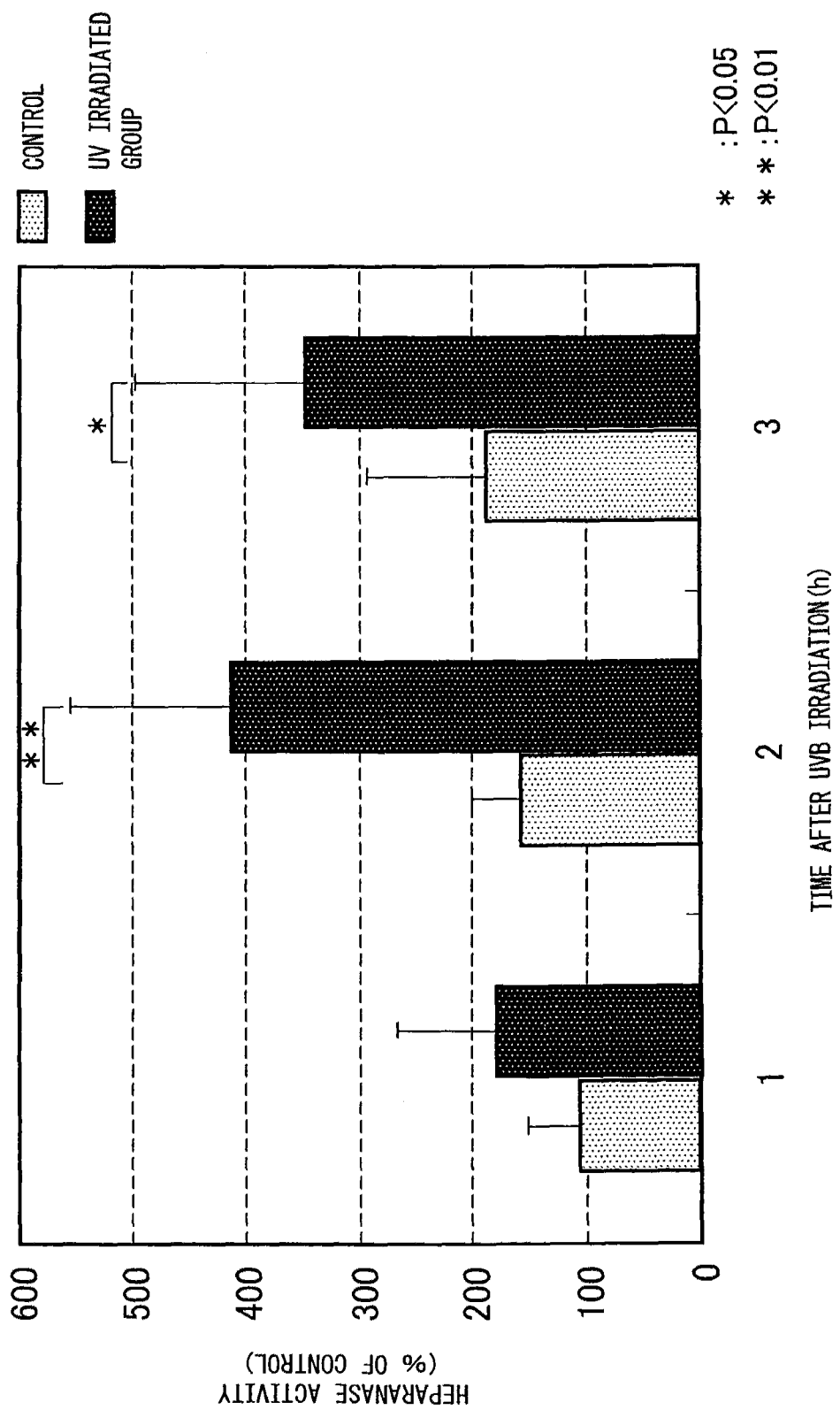
FIG. 1 is a graph showing the difference in heparanase activity in normal human keratinocytes, under ultraviolet-irradiated and non-irradiated conditions.

The present inventors have searched for substances that can efficiently inhibit heparanase activity and have screened for various compounds as indicators of heparanase activity inhibition, and as a result have completed this invention upon finding specific resorcinol derivatives that significantly suppress heparanase activity.

It has been completely unknown in the prior art that resorcinol derivatives exhibit inhibiting action on heparanase activity. JP-H2-49715A and JP2006-124358A disclose the use of specific resorcinol derivatives as skin whiteners, and JP2007-254412A discloses the use of specific resorcinol derivatives in external preparations for skin for prevention or improvement of wrinkles, but these publications contain no disclosure regarding the inhibiting effect on heparanase activity.

In particular, JP2007-254412A teaches that the presence of heparin (a type of heparan sulfate) in cells promotes disintegration of the fascicular structure of collagen and leads to wrinkle formation (see paragraph [0006]), and suggests that resorcinol derivatives reduce intracellular heparin thus preventing disintegration of the fascicular structure of collagen, but this is completely different from the inhibiting action on heparanase activity by the resorcinol derivatives disclosed in the present invention. That is, inhibition of heparanase activity according to the invention causes suppression of the decomposition of heparan sulfate chains of heparan sulfate proteoglycan, so that the abundance of heparan sulfate (heparin, etc.) in cells can be kept at a high level.

Specifically, a heparanase activity inhibitor of the invention contains a 4-alkylresorcinol represented by formula (I) as an active ingredient.

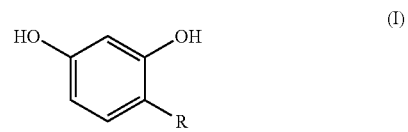

In the formula, R represents a C1-6 linear or branched alkyl group. Examples include methyl, ethyl, n-propyl, isopropyl, n-butyl, isobutyl, tert-butyl, n-pentyl, isopentyl, neopentyl, n-hexyl and sec-hexyl. Preferred among these are C2-4 linear or branched alkyl groups such as ethyl, n-propyl, isopropyl, n-butyl and isobutyl, and especially isobutyl. That is, the 4-alkylresorcinol of formula (I) is most preferably 4-isobutylresorcinol.

The method for producing the 4-alkylresorcinol of formula (I) is not particularly restricted, but there may be mentioned a method of Friedel-Crafts reaction between a saturated carboxylic acid or saturated carboxylic acid halide and resorcinol in the presence of a Lewis acid such as zinc chloride or aluminum chloride, and reduction of the resulting 4-acylresorcinol with zinc amalgam/hydrochloric acid (JP-H06-51619A and U.S. Pat. No. 2,093,778B), a method of using alumina as a catalyst for reaction between resorcinol and n-hexanol in a liquid phase at 200-400° C. to directly produce 4-n-hexylresorcinol (GB1581428B), and a method of using one or more compounds selected from among specific metal oxides and hydroxides as catalysts for reaction of alcohol with resorcinol in a supercritical state to produce 4-alkylresorcinol (JP2002-167344A).

The heparanase activity inhibitor of the invention may contain a single 4-alkylresorcinol of formula (I) alone, but it may instead contain 2 or more 4-alkylresorcinols of formula (I) in any desired combination and proportion.

The content of the 4-alkylresorcinol of formula (I) in the heparanase activity inhibitor of the invention is not particularly restricted so long as it is an amount sufficient to effectively exhibit inhibition against heparanase activity, and it may be appropriately selected according to the purpose of the heparanase activity inhibitor. Generally, however, the proportion of the 4-alkylresorcinol of formula (I) with respect to the entire heparanase activity inhibitor is preferred to be usually at least 0.0001 mass % and especially at least 0.0001 mass %, and usually no greater than 1 mass % and especially no greater than 0.2 mass %. When two or more 4-alkylresorcinols of formula (I) are used, their total amount must satisfy the aforementioned range.

The heparanase activity inhibitor of the invention may also contain other desired components in addition to the 4-alkylresorcinol of formula (I), so long as they do not substantially impair the inhibiting effect of the 4-alkylresorcinol of formula (I) on heparanase activity. Other components include other compounds with inhibiting action on heparanase activity (other active components), or medically acceptable carriers and/or adjuvants. Such other components may be used alone, or 2 or more may be used in any desired combination and ratio.

The heparanase activity inhibitor of the invention may be used as a cosmetic, quasi drug, pharmaceutical composition or the like, or as a compounding ingredient therein, although this is not restrictive.

A pharmaceutical composition containing a heparanase activity inhibitor of the invention as an active ingredient (a pharmaceutical composition of the invention) can be used for treatment, improvement or prevention of a condition or symptom associated with heparanase activity. Here, the "condition or symptom associated with heparanase activity" may be, for example, skin aging, cancer cell proliferation or metastasis, angiogenesis, or the like. Thus, the pharmaceutical composition of the invention may be suitably used, for example, for improvement or prevention of skin aging (anti-aging), suppression of cancer cell proliferation or metastasis, or suppression of angiogenesis.

Natural aging is a major cause of skin aging from a macroscopic viewpoint, but other causes such as oxidation, dryness and sunlight (ultraviolet rays) are also direct factors related to skin aging. The specific phenomenon of skin aging is known to be associated with cellular damage due to reduction in mucopolysaccharides including hyaluronic acid, collagen crosslinking reaction and ultraviolet rays.

A great deal of research is being carried out with the aim of inhibiting or improving skin wrinkles, fine wrinkles, sagging and the like, caused by skin damage or skin aging due to ultraviolet exposure. As a result, efficacy has been demonstrated for promoting hyaluronic acid production (JP2001-163794A), suppressing production and activation of matrix metalloproteinases (MMP) (JP2000-503660X), promoting production of collagen and inhibiting esterase activation (JP-H11-335235A), suppressing angiogenesis (WO03/84302 and Japanese Patent Application No. 2003-581562), and suppressing lymphangiectasis (K. Kajiya et al., Am. J. Pathol., 2006, 169(4): 1496-1503).

Such research is largely divided into efforts to prevent and improve fine wrinkles, with focus on the epidermis or epidermal cells, and efforts to prevent and improve large wrinkles, with focus on suppressing changes in the dermis including blood vessels or lymphatic vessels. Propagation of changes in the epidermis to the dermis leads to alteration of the dermis, including the blood vessels and lymphatic vessels, and heparanase is intricately involved in the process.

The present inventors have in fact previously demonstrated that a significant anti-wrinkle effect is obtained by coating a fine wrinkle model with a heparanase activity inhibitor (PCT/JP2009/056717).

As explained in detail in the examples, the present inventors have demonstrated that irradiation of cultured normal keratinocytes with ultraviolet rays results in activation of the heparanase of the normal keratinocytes (see FIG. 1). It was also demonstrated that irradiation of human skin with ultraviolet rays increases the amount of heparanase in the epidermis, and reduces heparan sulfate in the basal membrane (see FIG. 2). It was thereby shown that heparanase activation occurs not only in fine wrinkle models but also by ultraviolet rays.

In addition, since basal membrane heparan sulfate is decomposed upon activation of heparanase, the present inventors prepared, as pseudo-skin models, a normal model containing heparan sulfate in a basal membrane and a heparan sulfate-decomposed model containing no heparan sulfate in the basal membrane, and evaluated VEGF permeability and angiogenesis. As a result, it was shown that VEGF permeability was increased and angiogenesis was induced in the heparan sulfate-decomposed model, compared to the normal model (see FIGS. 3 to 6).

Yano et al. have previously indicated that ultraviolet ray-induced induction of angiogenesis in the dermis and alteration of the dermis are important for formation of large wrinkles (Japanese Patent Application No. 2002-580892), and have found that heparanase is an enzyme intricately involved in not only fine wrinkles but also large wrinkles. That is, inhibition of heparanase activity is effective for not only preventing fine wrinkles due to dryness but also large wrinkles due to prolonged sun exposure.

The term "anti-aging", as used herein, means preventing and improving wrinkles, sagging and hardening of skin by suppressing alteration of skin caused by release of heparan sulfate-binding growth factors due to decomposition of proteoglycan heparan sulfate in the basal membrane by aging or photoaging, and specifically suppressing epidermal differentiation abnormalities, dermis angiogenesis, lymphangiectasis and elastin breakdown, to maintain an elastic, youthful and healthy state of skin.

The route of administration and dosage form of the pharmaceutical composition of the invention are not restricted, and may be selected as appropriate for the purpose. Examples of routes of administration include oral administration, parenteral administration (such as intravenous administration and intraperitoneal administration), local administration (such as skin application) and the like. For oral administration, the dosage form may be a solid preparation such as a tablet, coated tablet, sugar-coated tablet, granules, powder, capsule (for example, a hard or soft gelatin capsule), or a liquid preparation (solution or suspension) such as an internal liquid drug or syrup. For a parenteral administration, it may be in the form of an injection or the like. For local administration, it may be a form in which a solution system, solubilized system, emulsified system, powder-dispersed system, water/oil two-layer system, water/oil/powder three-layer system or the like, is prepared as a patch, ointment, cream, latex, cosmetic water, gel or aerosol.

The content of the heparanase activity inhibitor of the invention in a pharmaceutical composition of the invention is also not restricted, and may be appropriately selected according to the purpose, dosage form and route of administration of the pharmaceutical composition. When the pharmaceutical composition of the invention is an external preparation for skin, for example, the content of the heparanase activity inhibitor of the invention is preferred to be usually in the range of at least 0.0001 mass %, and especially at least 0.0001 mass %, and usually no greater than 1 mass % and especially no greater than 0.2 mass %, as the dry mass (solid mass) of the total external preparation for skin. If the content is less than this range, the effect of the heparanase activity inhibitor of the invention will tend to be insufficient, and if it exceeds this range, no further effect may be expected commensurate with the increased content, and formulation will also tend to become difficult.

The pharmaceutical composition of the invention may also contain one or more other desired components in addition to the heparanase activity inhibitor of the invention, so long as the inhibiting effect on heparanase activity by the heparanase activity inhibitor of the invention is not substantially impaired. There are no particular restrictions on such other components, and they may be appropriately selected according to the purpose, dosage form and route of administration of the pharmaceutical composition, but medically acceptable carriers and/or adjuvants may be mentioned as examples. Examples of adjuvants include diluents, binders, disintegrators, thickeners, dispersing agents, reabsorption accelerators, taste correctives, buffering agents, surfactants, dissolving aids, preservatives, emulsifiers, isotonizing agents, stabilizers and pH regulators.

As specific examples, when the pharmaceutical composition of the invention is to be used as an external preparation for skin, components commonly used in external preparations, such as skin whiteners, humectants, antioxidants, oil components, ultraviolet absorbers, surfactants, thickeners, alcohols, powder constituents, coloring agents, aqueous components, water or various skin nutrient preparations, may be appropriately added as necessary. In addition, there may also be added appropriate amounts of metal ion chelators such as disodium edetate, trisodium edetate, sodium citrate, sodium polyphosphate, sodium metaphosphate or gluconic acid, antiseptic agents such as methylparaben, ethylparaben or butylparaben, caffeine, tannin, verapamil, tranexamic acid or their derivatives, licorice extract, drug agents such as glabridin, Chinese quince fruit hot water extract, galenicals, tocopherol acetate, glycyrrhizic acid and its derivatives or salts, skin whiteners such as vitamin C, magnesium ascorbate phosphate, glucoside ascorbate, arbutin or kojic acid, saccharides such as glucose, fructose, mannose, sucrose or trehalose, and vitamin A derivatives such as retinoic acid, retinol, retinol acetate or retinol palmitate.

On the other hand, when the heparanase activity inhibitor of the invention is to be used in a cosmetic or quasi drug, it is preferably used as an active ingredient of a wrinkle improving agent. A wrinkle improving agent containing the heparanase activity inhibitor of the invention as an active ingredient (a wrinkle improving agent of the invention) may be used to prevent or suppress formation of wrinkles. As mentioned above, wrinkles are largely classified as fine wrinkles formed in the epidermis by dryness and the like, and large wrinkles formed in the dermis by ultraviolet rays and the like, and a wrinkle improving agent of the invention may be applied to either type and is particularly effective for improving large wrinkles caused by ultraviolet rays.

The route of administration and dosage form of the wrinkle improving agent of the invention are not restricted, and may be selected as appropriate for the purpose. Oral administration and local administration may be mentioned as examples of routes of administration. Examples of dosage forms include the various dosage forms mentioned above, for a pharmaceutical composition, and addition to foods or beverages, for oral administration.

The content of the heparanase activity inhibitor of the invention in a wrinkle improving agent of the invention is also not restricted, and may be appropriately selected according to the purpose, dosage form and route of administration of the wrinkle improving agent.

The wrinkle improving agent of the invention may also contain one or more other desired components in addition to the heparanase activity inhibitor of the invention, so long as the inhibiting effect on heparanase activity by the heparanase activity inhibitor of the invention is not substantially impaired. There are no particular restrictions on other components, and they may be appropriately selected according to the purpose of use, the dosage form and the route of administration of the wrinkle improving agent.

The present invention has been explained with concrete examples, with the understanding that these are merely for illustration and that the invention may incorporate any desired modifications that fall within the scope of the claims of the invention.

The present invention will now be explained in greater detail with reference to examples, with the understanding that the invention is not meant to be limited to these examples.

EXAMPLES

Example 1

Evaluation Based on Heparanase Activity Inhibition Rate

A431 cells (human epithelial carcinoma cells) were cultured in 10% serum-containing DMEM (Dulbecco's modified Eagle medium). The cultured cells were solubilized in lysis buffer (50 mM Tris, 0.5% TritonX-100, 0.15 M sodium chloride, pH 4.5) and collected with a scraper, and then pipetted and allowed to stand on ice for 30 minutes. This was followed by centrifugation at 10,000 rpm for 10 minutes to remove the insoluble portion, and the supernatant was recovered as cell extract. The amount of protein in the cell extract was measured with a BCA protein assay kit (BCA Protein Assay Kit, PIERCE, Calif. 46141).

The A431 cell extract was then diluted to 500 µg/mL with assay buffer (50 mM HEPES, 50 mM sodium acetate, 150 mM sodium chloride, 9 mM calcium chloride, 0.1% BSA). Next, the test compound was dissolved in DMSO and added to the diluted cell extract in proportions of 0.0005 mass %, 0.005 mass % and 0.05 mass %, and these were mixed to prepare sample solutions (DMSO final concentration: 5%). A control solution was prepared by mixing DMSO with the diluted cell extract to a final concentration of 5%. The sample solution and control solution were each seeded in a biotinylated heparan sulfate-immobilized plate at 100 µL/well. After reaction at 37° C. for 2 hours and rinsing 3 times with PBS-T, 10,000-fold diluted HRP-avidin (Vector, A-2004)/PBS-T was added at 100 µL/well, and reaction was continued at 37° C. for 1 hour. After further rinsing 3 times with PBS-T, TMB reagent (BIO-RAD, 172-1066) was added at 100 µL/well and reacted therewith, the reaction was terminated with 1N sulfuric acid, and the absorbance at 475 nm (OD475) was measured.

Also, DMSO was added to a serial diluent prepared with the aforementioned A431 cell extract assay buffer (cell extract concentrations: 500 µg/mL, 50 µg/mL, 5 µg/mL, 0.5 µg/mL), to a final concentration of 5% without addition of the test compound, to obtain a mixture (solution for calibration curve). The solution for the calibration curve was subjected to treatment by the same procedure described above, from seeding of the biotinylated heparan sulfate-immobilized plate, and the OD475 was measured.

Next, a calibration curve for protein concentration was drawn based on the OD475 value of the solution for the calibration curve, and this calibration curve was used to calculate the protein concentration of each sample solution from the OD475 value of a sample solution obtained by adding the test compound at different addition concentrations. The protein concentration was calculated in the same manner for the control solution. The heparanase activity inhibition rate of each sample solution was determined from the ratio of the protein concentration of each sample solution and the protein concentration of the control solution (%).

The details regarding this procedure are described in JP2003-502054X.

The heparanase activity inhibiting effect of 4-isobutylresorcinol was tested by the procedure described above. The results are shown in Table 1. Table 1 shows that 4-isobutylresorcinol exhibits an inhibition rate of 37.64% even at an addition concentration of 0.0005%, and 94.74% at an addition concentration of 0.05%, and thus effectively inhibits heparanase activity.

TABLE 1

| Heparanase activity inhibition rates | | |
|---|---|---|
| Compound | Added concentration | Inhibition rate |
| 4-Isobutylresorcinol | 0.0005% | 37.64% |
| 4-Isobutylresorcinol | 0.005% | 75.98% |
| 4-Isobutylresorcinol | 0.05% | 94.74% |

Example 2

Evaluation of Change in Heparanase Activity by Ultraviolet Radiation

Normal human keratinocytes were cultured with EpiLife normal keratinocyte medium. The culture medium was temporarily stationed in PBS and then irradiated with 50 mJ UVB, and after culturing for 1 hour, 2 hours and 4 hours, the cells were solubilized with lysis buffer and used as sample solutions in the ultraviolet irradiation group. Also, medium was temporarily stationed in PBS without ultraviolet irradiation, for use as a control solution. The sample solutions and control solution were used for treatment in the same manner as Example 1, and the OD475 was measured. The heparanase activities were evaluated in the same manner as Example 1, based on the obtained OD475 values. The results are shown in FIG. 1. It was shown that heparanase was significantly activated in the ultraviolet irradiation group compared to the non-irradiated control.

Figure 2:
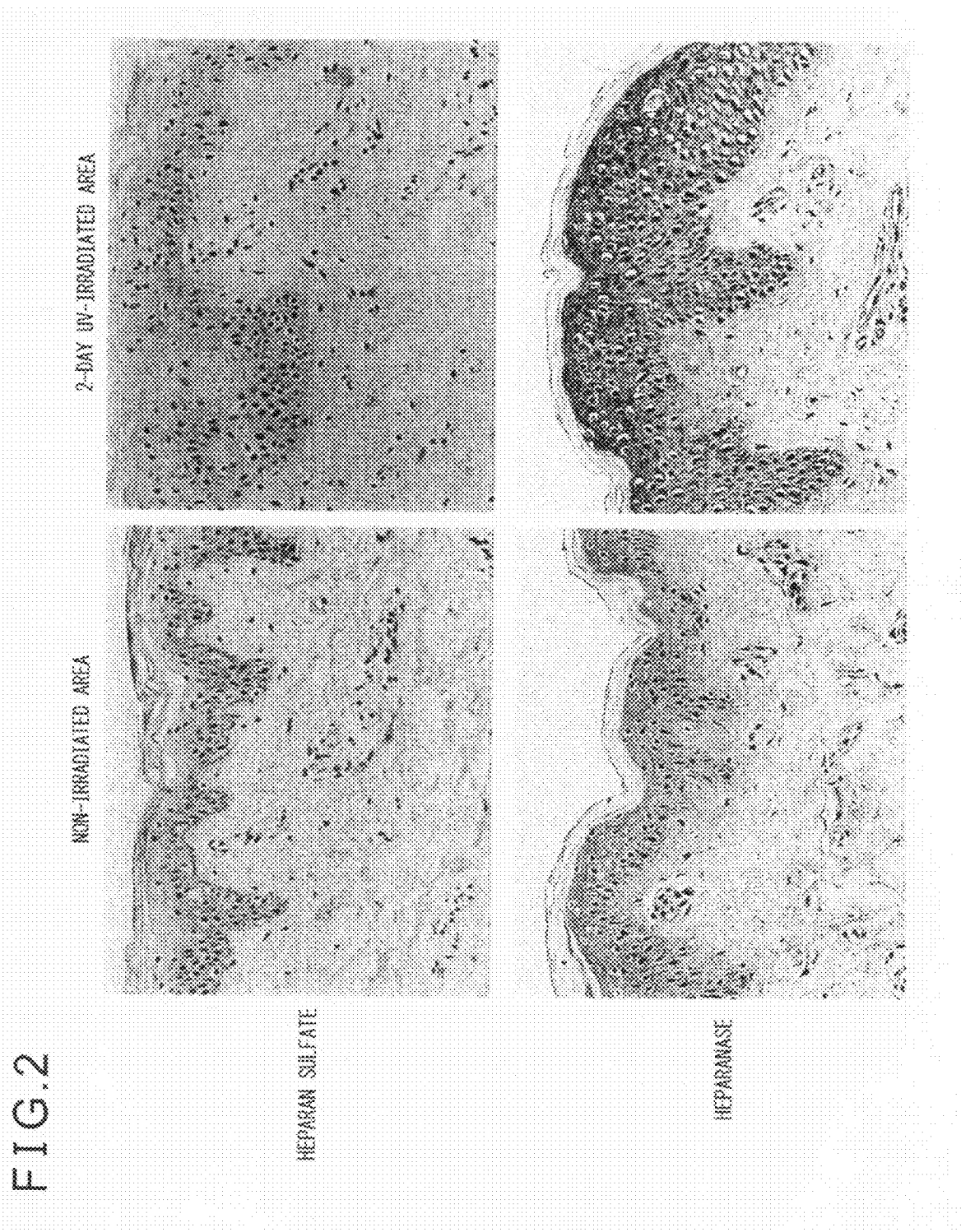
FIG. 2 is a set of immunostaining images for heparanase and heparan sulfate in ultraviolet-irradiated and non-irradiated sections of normal human buttock tissue.

Immunostaining of Heparanase and Heparan Sulfate in Ultraviolet-Irradiated Human Skin Human buttock skin (20-year-old) was irradiated with 2MED ultraviolet rays, and after 2 days the irradiated section and surrounding non-irradiated buttock skin were biopsied, and a paraffin block was formed by the AMeX method. A 3 µm tissue section was formed, and the heparanase and heparan sulfate were immunostained. The obtained immunostaining image is shown in FIG. 2. The amount of heparanase was clearly increased and the heparan sulfate content was reduced in the ultraviolet irradiated section, compared to the non-irradiated section.

Figure 3:
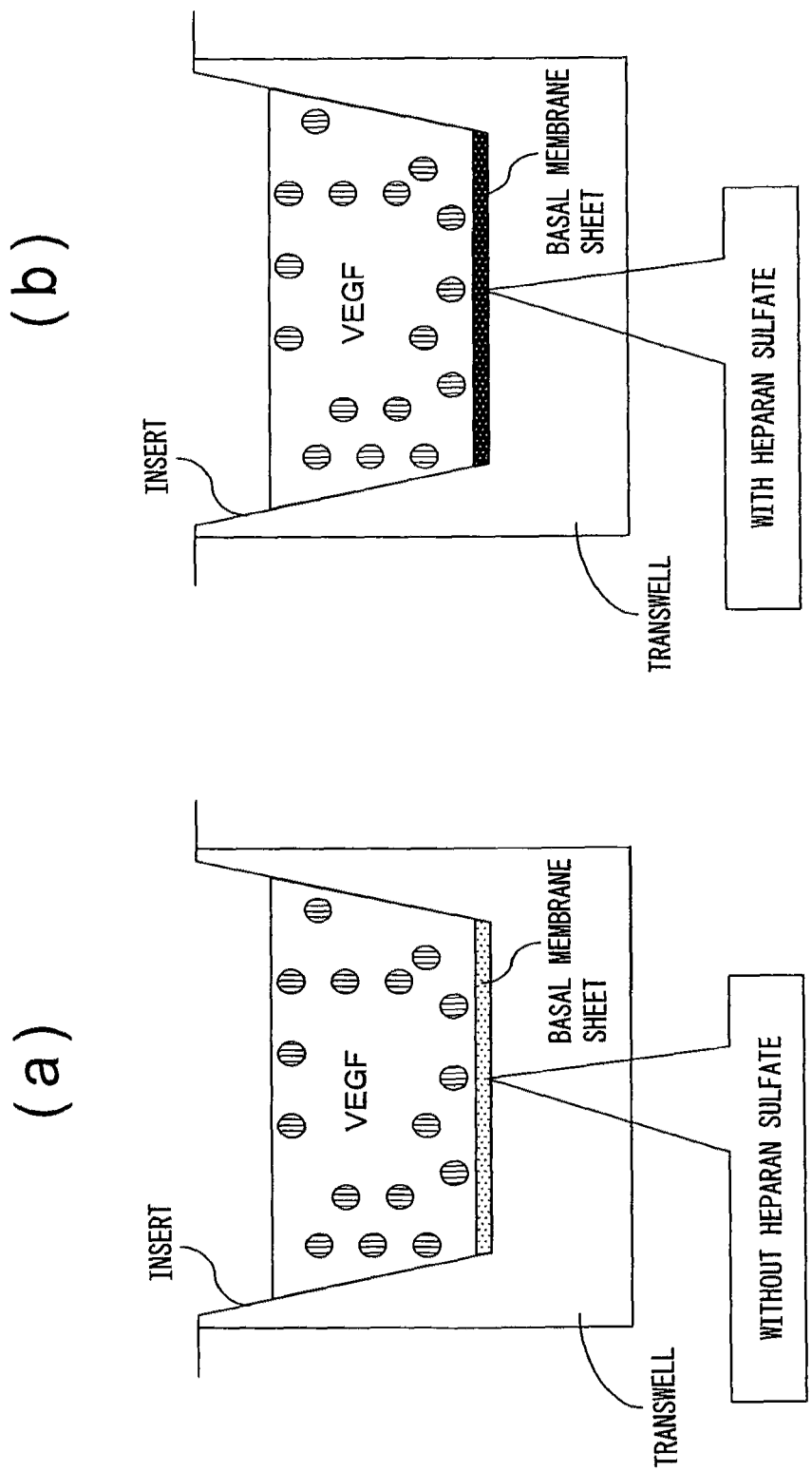
FIGS. 3(a) and 3(b) are both schematic diagrams of pseudo-skin models, where

Evaluation of VEGF Permeability and Angiogenesis with and without Heparan Sulfate After heating and dissolving 2 mg of heparan sulfate and 10 mg of agarose in 1 ml of PBS (1% agarose solution), it was coated with an insert (24-well Transwell by Corning, Inc.) to form a heparan sulfate-containing sheet. As a control, a sheet containing no heparan sulfate was formed by the same procedure, except that agarose alone was used, without using heparan sulfate. The insert interior was selected for the epidermis side, the sheet as the basal membrane, and the well on the dermis side, to prepare a pseudo-skin model (FIG. 3$a,b$).

The obtained pseudo-skin model can be used as an evaluation system for evaluating VEGF permeability and angiogenesis, based on the presence or absence of heparan sulfate in the sheet selected as the basal membrane (hereinafter referred to as "basal membrane sheet"). In the explanation which follows, the pseudo-skin model containing heparan sulfate in the basal membrane sheet is referred to as the "normal model", and the pseudo-skin model containing no heparan sulfate in the basal membrane sheet is referred to as the "heparan sulfate-decomposed model".

First, for evaluation of the VEGF permeability, a 10 µg/mL VEGF aqueous solution was added to the epidermis side (insert interior) of each model and allowed to stand for 3 hours at room temperature, and the VEGF concentration in the well on the dermis was detected with a VEGF ELISA kit (R&D systems). The results are shown in FIG. 4. The VEGF permeation was significantly reduced in the normal model compared to the heparan sulfate-decomposed model.

Figure 5:
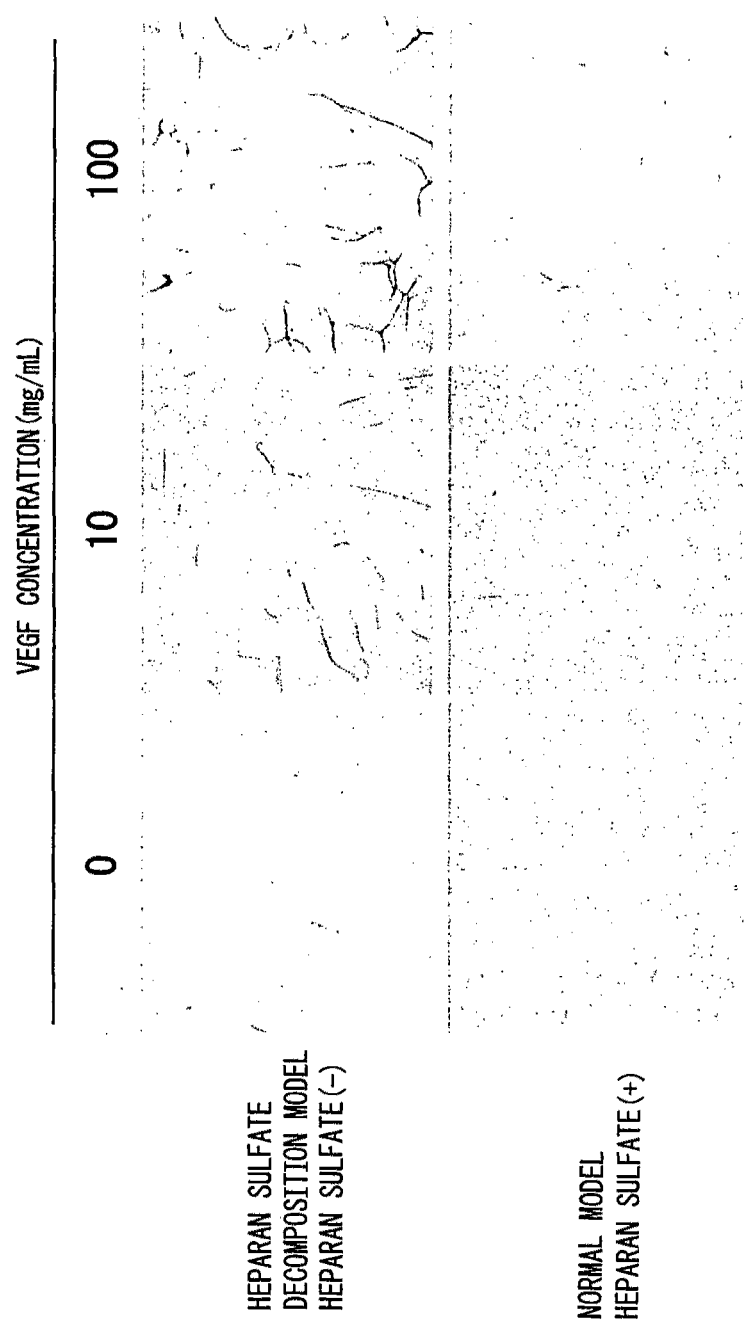
FIG. 5 is a set of photographs showing evaluation results for angiogenesis using the pseudo-skin models of FIGS. 3(a) and 3(b)

Next, for evaluation of angiogenesis, a 100 µg/mL VEGF aqueous solution was added to the epidermis side (insert interior) of each model, and set in an angiogenesis kit (Kurabo Industries, Ltd.) for culturing for 11 days, after which an optical microscope photograph of the culture was taken. The obtained image is shown in FIG. 5. Notable angiogenesis was observed in the heparan sulfate-decomposed model in a concentration dependent manner, while no angiogenesis was observed in the normal model.

Figure 6:
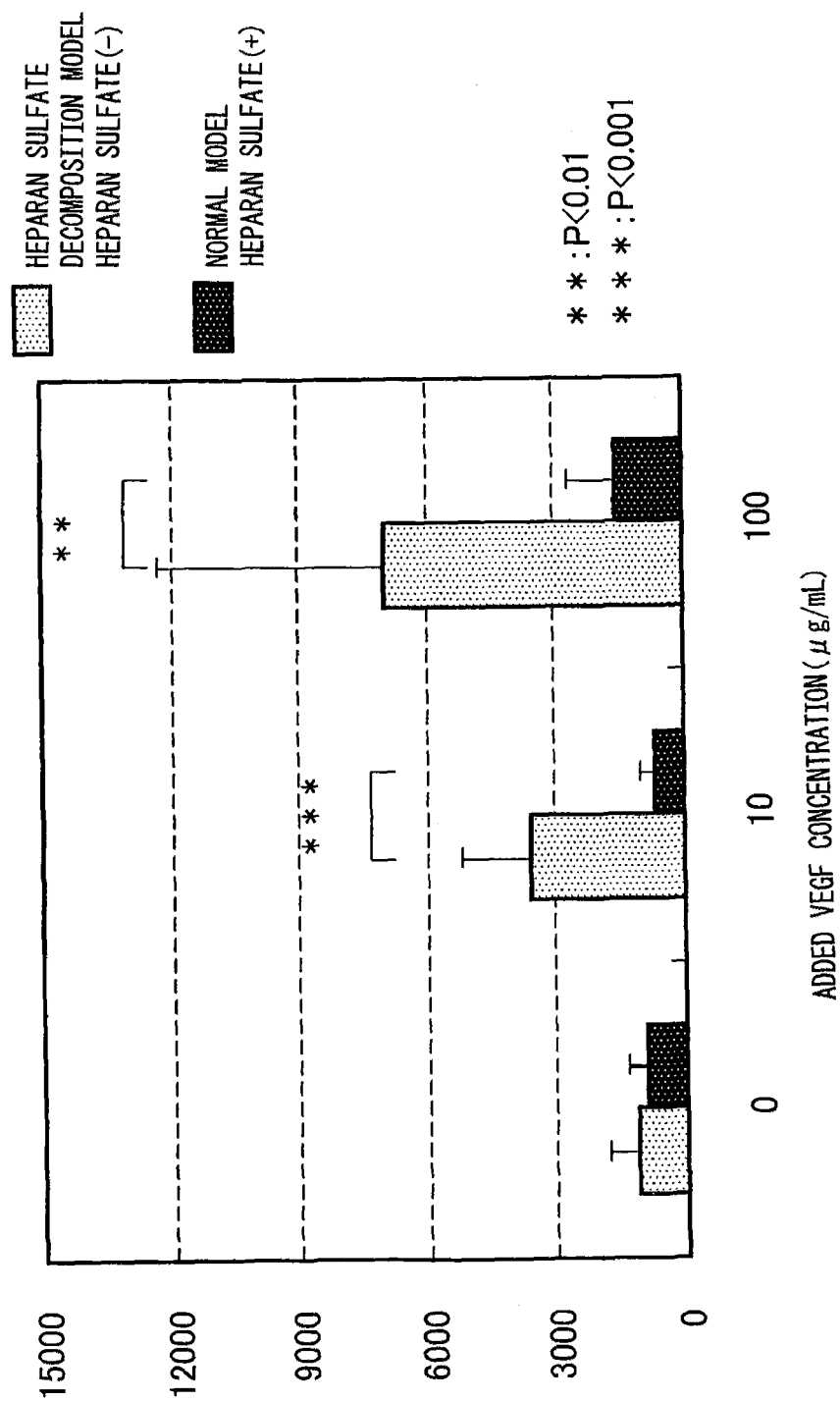
FIG. 6 is a graph showing analysis results for blood vessel area in the photograph of FIG. 5.

Angiogenesis kit analysis software (Kurabo Industries, Ltd.) was used to analyze the blood vessel area in the image of FIG. 5. The results are shown in FIG. 6. A notable increase in blood vessel area was observed in the heparan sulfate-decomposed model compared to the normal model, demonstrating significant angiogenesis.

INDUSTRIAL APPLICABILITY

The present invention can be suitably used in fields of pharmaceutical compositions and the like, for the purpose of treatment, improvement or prevention of conditions or symptoms associated with heparanase activity, and specifically for improvement or prevention of skin aging (anti-aging), for wound healing, for suppression of proliferation or metastasis of cancer cells, and for suppression of angiogenesis.

The invention claimed is:

1. A method for suppressing formation of wrinkles caused by a reduced level of heparan sulfate in an epidermal basal membrane, comprising administering, to a subject in need thereof, an effective amount of 4-isobutylresorcinol as an active ingredient.

2. A method for inhibiting heparanase activity, comprising administering, to a subject in need thereof, 4-isobutylresorcinol as an active ingredient.

3. The method according to claim 1, wherein heparanase activity is inhibited by the administration of the 4-isobutylresorcinol.

4. The method according to claim 1, wherein the 4-isobutylresorcinol is administered by oral administration, parenteral administration or local administration.

5. The method according to claim 3, wherein the 4-isobutylresorcinol is administered by oral administration, parenteral administration or local administration.

6. The method according to claim 4, wherein 4-isobutylresorcinol is present in an external preparation for skin in the range of at least 0.0001 to 1 mass %, as the dry mass of the total external preparation.

7. The method according to claim 5, wherein 4-isobutylresorcinol is present in an external preparation for skin in the range of at least 0.0001 to 1 mass %, as the dry mass of the total external preparation.

* * * * *